United States Patent [19]

Albers et al.

[11] 4,430,163

[45] Feb. 7, 1984

[54] PROCESS FOR THE CONTINUOUS SEPARATION OF SLIGHTLY VOLATILE COMPONENTS FROM A CRUDE PHTHALIC ACID ANHYDRIDE

[75] Inventors: Manfred Albers, Dortmund; Gerhard Keunecke, Geyen; Herbert Krimphove, Pulheim, all of Fed. Rep. of Germany

[73] Assignee: Davy McKee Aktiengesellschaft, Frankfurt, Fed. Rep. of Germany

[21] Appl. No.: 331,234

[22] Filed: Dec. 16, 1981

[30] Foreign Application Priority Data

Dec. 17, 1980 [DE] Fed. Rep. of Germany ....... 3047489
Aug. 22, 1981 [DE] Fed. Rep. of Germany ....... 3133310

[51] Int. Cl.³ .............................................. B01D 3/06
[52] U.S. Cl. ...................................... 203/75; 203/77; 203/88; 203/93; 549/250

[58] Field of Search ................. 260/346.7; 203/71, 73, 203/75, 77, 78, 80, 81, 82, 84, 88, 91, 94, 21, 93, 22-27

[56] References Cited

U.S. PATENT DOCUMENTS

| | | |
|---|---|---|
| 3,011,955 | 12/1961 | Brown .................................. 203/88 |
| 3,380,896 | 4/1968 | Scheiber et al. . |
| 3,655,521 | 4/1972 | Gehrken et al. ................. 260/346.7 |
| 3,699,008 | 10/1972 | Brendt et al. .................... 260/346.7 |
| 3,886,050 | 5/1975 | Deutner et al. ................. 260/346.7 |

FOREIGN PATENT DOCUMENTS 1807039 11/1968 Fed. Rep. of Germany .

Primary Examiner—Frank Sever
Attorney, Agent, or Firm—Bernard, Rothwell & Brown

[57] ABSTRACT

A process is provided for the continuous separation of slightly volatile components from a crude phthalic acid anhydride wherein a portion of the crude phthalic acid anhydride is compressed and heated before being reintroduced into a flash evaporator.

17 Claims, 1 Drawing Figure

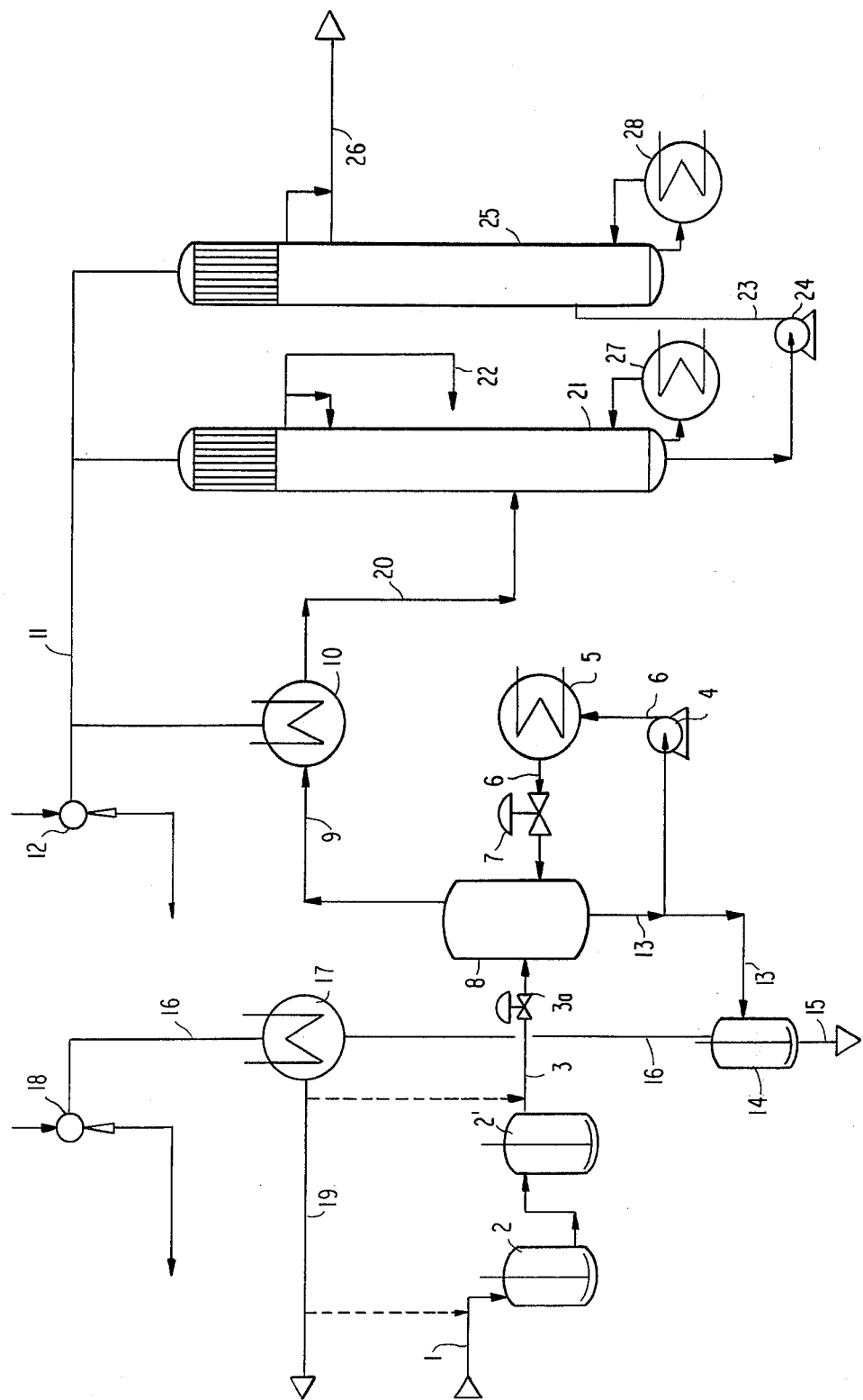

PROCESS FOR THE CONTINUOUS SEPARATION OF SLIGHTLY VOLATILE COMPONENTS FROM A CRUDE PHTHALIC ACID ANHYDRIDE

BACKGROUND OF THE INVENTION

1. Field of the Invention

This invention concerns a process for the continuous separation of slightly volatile components from a thermally pre-treated crude phthalic acid anhydride, produced by naphthalene oxidation, before its pure distillation.

2. Description of the Prior Art

Crude phthalic acid anhydride contains varying amounts of non-volatile impurities of different kinds depending on the initial substance from which it was produced and on the oxidation process which was used for its production. These impurities interfere, for different reasons, in the purification of the crude product by rectification. Therefore, in conventional processes, the crude product is subjected to a thermal pre-treatment before the rectification, and as a result of such thermal pretreatment, dibasic acids are transformed into their anhydrides, mono-carboxylc acids are decarboxylated and naphthoquinone is transformed into higher-molecular weight products which are non-volatile or only slightly volatile impurities. While the portion of the high-molecular weight impurities is low in the case of a crude oxidation product of o-xylol, and practically no problems arise in the rectification of such a product; crude phthalic acid anhydride produced from naphthalene contains, among other ingredients, generally 1.0 to 1.3 percent by weight of non-volatile impurities and up to 0.5 percent by weight naphthoquinone. Since the naphthoquinone is transformed into higher-molecular weight products, which are impurities of low volatility, the phthalic acid anhydride finally supplied to the rectification may contain up to about 2 percent by weight of non-volatile impurities. As used herein, the terms non-volatile impurities and impurities refer to impurities that are non-volatile or only slightly volatile under the conditions of temperature and pressure involved in the described process.

It has been determined that these impurities can interfere in the continuous rectification of crude phthalic acid anhydride, which is generally performed in two stages. Such interference is caused by the settling of the impurities on the heating surfaces of the evaporators connected to the rectification column. As a result of this interference, the operation is generally periodically interrupted in order to clean the evaporators. To resolve this problem, it has been proposed to initially subject the crude phthalic acid anhydride to distillation in batches, in order to separate the impurities from the phthalic acid anhydride. (DE-AS No. 1,668,398). Alternatively, a three-stage distillation of phthalic acid anhydride from naphthalene has been described in connection with a continuous operating method where, in the first stage, the impurities are separated initially by evaporating the crude product (H. Suter, *Phthalic Acid Anhydride and Its Use*, 1972, P. 45). In this three-stage method, a concentration of the impurities occurs in the first evaporation stage which leads quickly to a deposit on the heating surfaces. Finally, it is known to initially distill the pre-treated, liquid crude phthalic acid anhydride under reduced pressure, then to process the distillation residue in a separate residue distillation and to combine the distillates of the two procedures. With this operating method, the crude product must be heated to a high temperature, i.e., 450° C., in order to achieve a quantitative evaporation of the phthalic acid anhydride from the crude product. The high temperature favors the decomposition of phthalic acid anhydride and causes a reduction in the yield of the pure product. Furthermore, a correspondingly high pressure is required with the heating to 450° C. in order to keep the crude product in a liquid state in the heat exchanger, resulting in a need for additional equipment. If one would not apply the increased pressure, the phthalic acid anhydride would start boiling in the exchanger whereby impurities would again separate on the heat exchanger surfaces (German Disclosure Publication No. 1,295,540 corresponding to U.S. Pat. No. 3,380,896).

OBJECTS OF THE INVENTION

An object of this invention is to provide a process for the continuous separation of the impurities from thermally pre-treated crude phthalic acid anhydride, produced by naphthalene oxidation, which avoids the disadvantages resulting from the separation of impurities on the evaporator heating surfaces during rectification. In particular, coating of the heating surfaces which normally occurs with a preliminary separation of the impurities is avoided. A further object of this invention is to enable distillation to be carried out without requiring complex equipment.

SUMMARY OF THE INVENTION

These and other objects are accomplished in accordance with this invention by introducing heated crude phthalic acid anhydride into a flash evaporator, removing residue from the flash evaporator remaining after evaporation, compressing and heating a first portion of the residue and recirculating it to the flash evaporator.

The first portion of the crude phthalic acid anhydride residue removed from the flash evaporator is compressed to a pressure in the range from 1 to 5 bar and is heated to a temperature below the boiling point under the prevailing pressure and is returned to the flash evaporator. A second portion of the drained phthalic acid anhydride is supplied to a conventional residue distillation vessel for distillation and recirculation.

DETAILED DESCRIPTION OF THE INVENTION

According to one embodiment of this invention, the heated crude phthalic acid anhydride is subjected to a thermal pretreatment whereby it is preferably heated to a temperature in the range from 220° C. to 285° C. The percentage of phthalic acid anhydride evaporated will vary depending on the heating temperature and the pressure in the flash evaporator. Since the thermal content of the pretreated phthalic acid anhydride is not sufficient for the complete evaporation of the phthalic acid anhydride, even at a considerable vacuum in the flash evaporator, the remaining heat necessary to complete evaporation is supplied by circulating a portion of the remaining crude product residue through a heat exchanger. The circulating portion of phthalic acid anhydride residue is kept under a pressure in the area of the heat exchanger which prevents boiling. In this manner, the separation of impurities on the heating surfaces of the heat exchanger is avoided. Since the phthalic acid anhydride is compressed essentially for the purpose of avoiding boiling, the compression can naturally be effected at a higher pressure than 5 bar but this does not result in an advantage and leads to an operational disadvantage because of the greater compression work and the larger pump required. With lower percentages of evaporation per cycle, a correspondingly more frequent circulation of the crude product can be employed. Expediently, the compressed crude phthalic acid anhydride is cooled to a temperature in the range from 165° C. to 285° C. by the reduction in pressure in the flash evaporator.

Because of the flash evaporation, a residue forms in the sump of the flash evaporator which is highly concentrated with non-volatile impurities and still contains 20 to 80 percent by weight, preferably 50 to 70 percent by weight, phthalic acid anhydride. A portion of this residue fraction is separated in a residue distillation into an almost dry non-volatile fraction and a top product in a known manner. The residue distillation may be effected under a pressure in the range from 0.04 to 0.9 bar and the top product is again united with crude phthalic acid anhydride. The almost dry non-volatile fraction remaining after residue distillation may be discarded.

It is preferable to condense the distillate which evaporated from the flash evaporator by cooling and to subsequently purify it by two-stage rectification. The condensation is appropriately effected in a heat exchanger, which is also preferably kept under vacuum. The formation of deposits on the heating surfaces of the two rectification stages is considerably reduced as a result of the preliminary separation of the residue according to the invention. When the readily volatile impurities are separated in the first rectification stage and the pure phthalic acid anhydride passes over in the second rectification stage, the accumulation of impurities should take place in the sump of the second rectification stage. While these impurities must be drained in relatively short time intervals with the customary operating method in order to avoid deterioration of the heat transmission in the reboiler, such draining is infrequently necessary with the process according to this invention involving the preliminary separation of the impurities.

One embodiment of the process according to the invention is described below in greater detail with reference to the drawing.

As illustrated in the drawing, the crude phthalic acid anhydride supplied through line 1 passes initially through an agitator vessel cascade consisting of two agitator vessels 2, 2' in which the product is heated, for example, to 280° C. under atmospheric pressure. The product leaving the second agitator vessel 2' through the line 3 flows into the flash evaporator 8. By doing so, its pressure is reduced to the negative pressure prevailing in the flash evaporator when passing through the valve 3a. A spontaneous evaporation of a portion of the phthalic acid anhydride contained in the crude product occurs in the vessel. A residue with an increased content of non-volatile or only slightly volatile impurities remains and is drained from the sump of the flash evaporator 8. A first portion of the residue is compressed in the compressor 4, preferably to a pressure in the range from 1–5 bar, then it is supplied to the heater 5 through line 6 and is heated there. Finally, the circulated residue's pressure is reduced again to the negative pressure of the flash evaporator 8 when passing through throttle valve 7. When the compressed and heated first portion is returned to the flash evaporator, the flash evaporator is kept under reduced pressure, preferably under a pressure of about 0.04 to 0.9 bar. Heating the compressed portion of crude phthalic acid anhydride to a temperature in the range from 175° to 350° C., preferably to a temperature in the range from 200° C. to 300° C. is sufficient to result in evaporation of a substantial portion of the phthalic acid anhydride when that portion is recirculated to the flash evaporator. The flash evaporator 8 is connected to a general vacuum line 11 by means of line 9 in which the condenser 10 is arranged; said vacuum line is kept under vacuum by means of an ejector booster pump 12. The fraction which evaporated in the course of the pressure reduction process enters condenser 10 through line 9 and is condensed there.

A second portion of the residue from the flash evaporator 8 enters the agitated residue distillation vessel 14 through line 13. It is separated there under vacuum into an almost dry bottom product and into a top product rich in phthalic acid anhydride. The residue evaporation in the vessel 14 can be effected intermittently; however, preferably it is carried out continuously, for example, in a thin-layer evaporator with wipers passing over the heating surfaces or in a vessel with an agitator passing over the walls. These evaporation vessels have area heating through the jacket. The almost dry non-volatile bottom product is drained at 15. The vessel 14 is connected to an ejector booster pump 18 by line 16 in which a condenser 17 is located. The top product from the residue distillation vessel is condensed in the condenser 17 and led off through line 19. It can be combined with the crude product in line 1 or 3 or can be utilized in other ways.

The product which is condensed in the condenser 10 is fed through line 20 into the first column 21 of two-stage rectification section. The more volatile impurities are distilled off the phthalic acid anhydride in column 21 under a weak vacuum and drained through line 22. The bottom product of column 21 enters the vacuum column 25, in which the phthalic acid anhydride is distilled over, through line 23 with the aid of pump 24. The pure product is drained at 26. The heating surfaces of the evaporators 27 and 28 of the column 21 and 25, respectively, are largely protected against the formation of impurity deposits by the process of this invention.

This invention is further illustrated by the following example.

EXAMPLE 10,000 kg/h crude phthalic acid anhydride produced by naphthalene oxidation are processed in a system illustrated in the drawing. They flow through a cascade of two agitator vessels and are kept there at 250° C. for, in all, 12 hours. The crude product is then subjected to a reduction in pressure to 0.14 bar in a flash evaporator. During this process, about 1850 kg/h of the supplied crude product evaporate. The non-evaporated residue is drained from the sump of the vessel, and a first portion of the residue is compressed to about 2 bar and heated to 230° C., through heat exchange with a heat carrier liquid at 310° C., and is then again subjected to a pressure of 0.14 bar in the flash evaporator. A temperature of 210° C. develops in the flash evaporator. A second portion of the residue, 1667 kg/h, is supplied to the residue distillation vessel from the circulating flow before the compression and are separated there into 500 kg/h almost dry non-volatile fraction and 1167 kg/h top product rich in phthalic acid anhydride.

The gas phase product from the flash evaporator is drawn through a condenser and condensed there. 8333 kg/h of the liquid crude product are obtained from the condenser which are purified in a two-stage rectification system. In the first column, the more volatile impurities are distilled off in an amount of 10 kg/h at a top pressure of 200 mbar and 185° C. The sump product of the first column is rectified in a second rectification column with a top pressure of 330 mbar and a top temperature of 165° C. In this way, 8320 kg/h pure phthalic acid anhydride are obtained. 36 kg bottom product are removed from the sump of the second column in time intervals of 12 hours. After operating for 1000 hours in this manner, no formation of deposits of non-volatile or only slightly volatile impurities could be observed on the heating surfaces of the heated located in the compression train or of the evaporators connected to the rectification columns.

The invention is not limited to the illustrated design. For instance, the flash evaporator may be under the same pressure as the pre-treatment vessels so that no reduction in pressure is effected during the transition from the last pre-treatment vessel to the flash evaporator. The flash evaporator can then be under atmospheric pressure in which only the circulated compressed partial flow is subjected to a reduction in pressure.

What is claimed is:

1. In a process for the purification of a crude phthalic acid anhydride that contains slightly volatile impurities and is produced by oxidation of naphthalene, which process includes
    (a) subjecting said crude phthalic acid anhydride to a thermal pretreatment;
    (b) subjecting the thermally-pretreated crude phthalic acid anhydride to a first distillation in a flash evaporator to produce a distillate with elevated content of phthalic anhydride and a residue which contains slightly volatile impurities;
    (c) subjecting the distillate to rectification to obtain a purified phthalic acid anhydride; the improvements which comprise;
    (d) removing residue from the first distillation and compressing a first portion of the residue to a pressure of from 1 to 5 bar and heating the residue to a temperature below the boiling point under the prevailing pressure;
    (e) recirculating the heated compressed residue to said first distillation in the flash evaporator; and
    (f) subjecting a second portion of the residue to residue distillation in a residue distillation vessel said second portion being of sufficient magnitude to reduce the formation of deposits on evaporator heating surfaces during rectification of the distillate.

2. A process as recited in claim 1 wherein the pressure in said flash evaporator is maintained in the range from about 0.04 to 0.9 bar.

3. A process as recited in claim 1 or claim 2 wherein said first portion of crude phthalic acid anhydride is heated after compression to a temperature in the range of 175° C. to 350° C.

4. A process as recited in claim 3 wherein said first portion returned to said flash evaporator after compression and heating cools in said flash evaporator to a temperature in the range from 165° C. to 285° C.

5. A process as recited in claim 4 wherein said distillate is condensed by cooling and is purified by a two-stage distillation.

6. A process as recited in claim 5 wherein said residue distillation is carried out under a pressure of 0.04 to 0.9 bar to provide a top product which is combined with crude phthalic acid anhydride before it enters said flash evaporator.

7. A process as recited in claim 4 wherein said residue distillation is carried out under a pressure of 0.04 to 0.9 bar to provide a top product which is combined with crude phthalic acid anhydride before it enters said flash evaporator.

8. A process as recited in claim 3 wherein said distillate is condensed by cooling and is purified by a two-stage distillation.

9. A process as recited in claim 8 wherein said residue distillation is carried out under a pressure of 0.04 to 0.9 bar to provide a top product which is combined with crude phthalic acid anhydride before it enters said flash evaporator.

10. A process as recited in claim 3 wherein said residue distillation is carried out under a pressure of 0.04 to 0.9 bar to provide a top product which is combined with crude phthalic acid anhydride before it enters said flash evaporator.

11. A process as recited in claims 1 or 2 wherein said first portion returned to said flash evaporator after compression and heating cools in said flash evaporator to a temperature in the range from 165° C. to 285° C.

12. A process as recited in claim 11 wherein said fraction is condensed by cooling and is purified by a two-stage distillation.

13. A process as recited in claim 12 wherein said residue distillation is carried out under a pressure of 0.04 to 0.9 bar to provide a top product which is combined with crude phthalic acid anhydride before it enters said flash evaporator.

14. A process as recited in claim 11 wherein said residue distillation is carried out under a pressure of 0.04 to 0.9 bar to provide a top product which is combined with crude phthalic acid anhydride before it enters said flash evaporator.

15. A process as recited in claims 1 or 2 wherein said distillate is condensed by cooling and is purified by a two-stage distillation.

16. A process as recited in claim 15 wherein said residue distillation is carried out under a pressure of 0.04 to 0.9 bar to provide a top product which is combined with crude phthalic acid anhydride before it enters said flash evaporator.

17. A process as recited in claims 1 or 2 wherein said residue distillation is carried out under a pressure of 0.04 to 0.9 bar to provide a top product which is combined with crude phthalic acid anhydride before it enters said flash evaporator.

* * * * *